(12) United States Patent
Wang et al.

(10) Patent No.: US 8,846,990 B2
(45) Date of Patent: Sep. 30, 2014

(54) PROCESS FOR PRODUCING 2,3,3,3-TETRAFLUOROPROPENE

(71) Applicant: Honeywell International Inc., Morristown, NJ (US)

(72) Inventors: Haiyou Wang, Amherst, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 14/351,735

(22) PCT Filed: Oct. 10, 2012

(86) PCT No.: PCT/US2012/059441
§ 371 (c)(1),
(2), (4) Date: Apr. 14, 2014

(87) PCT Pub. No.: WO2013/055726
PCT Pub. Date: Apr. 18, 2013

(65) Prior Publication Data
US 2014/0235903 A1    Aug. 21, 2014

Related U.S. Application Data

(63) Continuation-in-part of application No. 13/287,199, filed on Nov. 2, 2011, now Pat. No. 8,455,704, and a continuation-in-part of application No. 12/167,159, filed on Jul. 2, 2008.

(60) Provisional application No. 61/547,330, filed on Oct. 14, 2011, provisional application No. 60/958,468, filed on Jul. 6, 2007.

(51) Int. Cl.
C07C 17/00    (2006.01)
C07C 17/38    (2006.01)
C07C 17/25    (2006.01)
C23G 5/00    (2006.01)
C07C 17/20    (2006.01)

(52) U.S. Cl.
CPC .............. C07C 17/25 (2013.01); C07C 17/38 (2013.01); C23G 5/00 (2013.01); C07C 17/20 (2013.01)
USPC ........................ 570/155; 570/156; 570/177

(58) Field of Classification Search
CPC .......... C07C 17/20; C07C 17/25; C07C 21/18; C07C 17/38
USPC ........................................ 570/155, 156, 177
See application file for complete search history.

(56) References Cited

U.S. PATENT DOCUMENTS

| | | | |
|---|---|---|---|
| 2,931,840 A | 4/1960 | Marquis et al. | |
| 5,162,594 A | 11/1992 | Krespan et al. | |
| 7,884,254 B2 | 2/2011 | Wang et al. | |
| 8,053,612 B2 | 11/2011 | Wang et al. | |
| 8,058,486 B2 | 11/2011 | Merkel et al. | |
| 8,119,557 B2 | 2/2012 | Wang et al. | |
| 8,648,222 B2 | 2/2014 | Wang et al. | |
| 8,691,720 B2 | 4/2014 | Wang et al. | |
| 2007/0197842 A1 | 8/2007 | Mukhopadhyay et al. | |
| 2009/0043136 A1 | 2/2009 | Wang et al. | |
| 2009/0240090 A1 * | 9/2009 | Merkel et al. | 570/160 |
| 2010/0048961 A1 | 2/2010 | Merkel et al. | |
| 2010/0123154 A1 | 5/2010 | Lee | |
| 2010/0331583 A1 * | 12/2010 | Johnson et al. | 570/156 |
| 2011/0105807 A1 | 5/2011 | Kopkalli et al. | |
| 2011/0270000 A1 | 11/2011 | Bektesevic et al. | |
| 2014/0113805 A1 | 4/2014 | Wang et al. | |

FOREIGN PATENT DOCUMENTS

WO    WO2010123154    10/2010

OTHER PUBLICATIONS

Banks, et al., "Preparation of 2,3,3,3-tetrafluoropropene from trifluoroacetylacetone and sulpher tetrafluoride"; Journal of Fluorine Chemistry 82 (1997) 171-174.
U.S. Appl. No. 14/206,587, filed Mar. 12, 2014.
U.S. Appl. No. 14/348,804, filed Mar. 31, 2014.
U.S. Appl. No. 14/351,735, filed Apr. 14, 2014.

\* cited by examiner

*Primary Examiner* — Jafar Parsa
(74) *Attorney, Agent, or Firm* — Scully, Scott, Murphy & Presser, P.C.

(57) ABSTRACT

The present invention relates, in part, to the discovery that the presence of impurities in a reactor for dehydrochlorinating HCFC-244bb to HFO-1234yf results in selectivity changeover from HFO-1234yf to HCFO-1233xf. By substantially removing such impurities, it is shown that the selectivity to HFO-1234yf via dehydrochlorination of HCFC-244bb is improved.

22 Claims, No Drawings

PROCESS FOR PRODUCING 2,3,3,3-TETRAFLUOROPROPENE

CROSS REFERENCES TO RELATED APPLICATIONS

This application claims priority to U.S. Provisional Application No. 61/547,330, filed Oct. 14, 2011, the contents of which are incorporated herein by reference.

This application is a continuation-in-part of U.S. application Ser. No. 13/287,199, filed on Nov. 11, 2011, the contents each of which are incorporated herein by reference.

This application is also is a continuation-in-part of U.S. application Ser. No. 12/167,159, filed Jul. 2, 2008, which claims priority to U.S. Provisional Application No. 60/958,468, filed Jul. 6, 2007, the contents each of which are incorporated herein by reference.

FIELD OF INVENTION

This invention relates to a process for preparing fluorinated organic compounds, more particularly to a process for preparing fluorinated olefins, and even more particularly to a process for producing 2,3,3,3-tetrafluoropropene (HFO-1234yf).

BACKGROUND OF THE INVENTION

Hydrofluoroolefins (HFOs), such as tetrafluoropropenes (including 2,3,3,3-tetrafluoropropene (HFO-1234yf)), are now known to be effective refrigerants, fire extinguishants, heat transfer media, propellants, foaming agents, blowing agents, gaseous dielectrics, sterilant carriers, polymerization media, particulate removal fluids, carrier fluids, buffing abrasive agents, displacement drying agents and power cycle working fluids. Unlike chlorofluorocarbons (CFCs) and hydrochlorofluorocarbons (HCFCs), both of which potentially damage the Earth's ozone layer, HFOs do not contain chlorine and, thus, pose no threat to the ozone layer. HFO-1234yf has also been shown to be a low global warming compound with low toxicity and, hence, can meet increasingly stringent requirements for refrigerants in mobile air conditioning. Accordingly, compositions containing HFO-1234yf are among the materials being developed for use in many of the aforementioned applications.

Several methods of preparing HFOs are known. For example, U.S. Pat. No. 4,900,874 (Ihara et al.) describes a method of making fluorine containing olefins by contacting hydrogen gas with fluorinated alcohols. Although this appears to be a relatively high-yield process, commercial scale handling of hydrogen gas at high temperature is hazardous. Also, the cost of commercially producing hydrogen gas, such as building an on-site hydrogen plant, is economically costly.

U.S. Pat. No. 2,931,840 (Marquis) describes a method of making fluorine containing olefins by pyrolysis of methyl chloride and tetrafluoroethylene or chlorodifluoromethane. This process is a relatively low yield process and a very large percentage of the organic starting material is converted to unwanted and/or unimportant byproducts, including a sizeable amount of carbon black which tends to deactivate the catalyst used in the process.

The preparation of HFO-1234yf from trifluoroacetylacetone and sulfur tetrafluoride has been described (See Banks, et al., Journal of Fluorine Chemistry, Vol. 82, Iss. 2, p. 171-174 (1997)). Also, U.S. Pat. No. 5,162,594 (Krespan) discloses a process wherein tetrafluoroethylene is reacted with another fluorinated ethylene in the liquid phase to produce a polyfluoroolefin product.

However, there remains a need for an economic means of producing hydrofluoroolefins, such as HFO-1234yf. The present invention satisfies this need among others.

SUMMARY OF THE INVENTION

The present invention relates, in part, to the surprising discovery that, during the dehydrochlorination of 2-chloro-1,1,1,2-tetrafluoropropane (HCFC-244bb) to HFO-1234yf in a reactor, impurities formed through halogenation of the materials of the reactor leads to selectivity changeover from HFO-1234yf to 2-chloro-3,3,3-trifluoropropene (HCFO-1233xf). Accordingly, the present invention relates to methods of improving HFO-1234yf selectivity by reducing the presence of impurities in the reactor, particularly, though not exclusively, during reactor shut-down and/or maintenance, or as caused by air or moisture in the feed materials. To this end, the presence of impurities is reduced and selectivity of the reaction to HFO-1234yf improved.

In one aspect, the present invention relates to a process for removing impurities from a reactor with an inner metal alloy surface such that the reactor is substantially free of impurities by (a) purging the reactor with an inert gas, (b) optionally, oxidizing the impurities in the reactor by introducing an oxidizing agent into the reactor under conditions effective to oxidize the impurities, (c) reducing the impurities in the reactor by introducing a reducing agent into the reactor under conditions effective to reduce the impurities, (d) cooling the reactor to an ambient temperature while passing the reducing agent and/or inert gas through the reactor, and (e) maintaining a positive pressure in the reactor with the reducing agent and/or the inert gas. As used herein, the definition of "substantially free" means that the amount of impurities in the reactor is reduced so as to measurably improve selectivity of the conversion of HCFC-244bb to HFO-1234yf and/or decrease selectivity in the conversion of HCFC-244bb to HCFO-1233xf. The impurities may include, but are not limited to, metal halides, metal oxides, and/or carbonaceous materials. The metal halides can comprise, for example, halides of Ni, Cr, Fe, Mo, Nb, Cu, and Co.

In certain embodiments, the inert gas introduced into the reactor in the purging step includes, for example, He, Ar, $N_2$, and combinations of these. In certain embodiments, the reactor is purged with the inert gas at a temperature of from about 100° C. to about 700° C., about 200° C. to about 600° C., about 300° C. to about 500° C., or about 400° C. to about 500° C. In one embodiment, purging is performed under conditions of continuous flow of inert gas. In another embodiment, the reactor is pressurized with inert gas and then depressurized for a few times sufficient to accomplish purging. Combinations of these embodiments may also be implemented.

In certain embodiments, the step of oxidizing impurities in the reactor includes introducing an oxidizing agent into the reactor under conditions effective to burn off the carbonaceous material in the reactor. Such oxidizing agents include, but are not limited to, $H_2O$, $CO_2$, $O_2$, air, $O_3$, $Cl_2$, $N_2O$, and combinations of these. In certain embodiments, the oxidation is carried out at a temperature of from about 100° C. to about 700°, about 200° C. to about 600° C., about 300° C. to about 500° C., or about 400° C. to about 500° C. In one embodiment, oxidizing occurs under conditions of continuous flow of oxidizing agent. In another embodiment, the oxidizing agent is diluted or provided in diluted form. Suitable diluents include inert gases such as $N_2$, Ar, and He. In one practice of this embodiment, the oxidizing agent is oxygen and is diluted with nitrogen. The dilution can be as high as practically possible, for example, about 0.1% volume of oxidizing agent. In a preferred embodiment, the concentration of oxidizing agent after dilution ranges from about 0.5 to about 21 vol %, preferably from 1 to about 5 vol %, and more preferably from about 2 to about 3 vol %.

In certain embodiments, the step of reducing impurities in the reactor includes introducing a reducing agent into the reactor under conditions effective to convert any metal halides or metal oxides into metallic metals. Such reducing agents may include, but are not limited to, $H_2$, $NH_3$, CO, and $C_1$-$C_{12}$ hydrocarbons and combinations of these. In certain embodiments, the reducing agent is diluted or provided in diluted form. Suitable diluents include inert gases such as $N_2$, Ar, and He. In one practice of this embodiment, the reducing agent is hydrogen and is diluted with nitrogen. The dilution can be as high as practically possible, for example, about 0.1% volume of reducing agent. In a preferred embodiment, the concentration of reducing agent after dilution ranges from about 0.5 to about 20 vol %, preferably from about 1 to about 5 vol %, and more preferably from about 2 to about 2.5 vol %. In certain embodiments, the reduction is carried out at a temperature of from about 100° C. to about 700°, about 200° C. to about 600° C., about 300° C. to about 500° C., or about 400° C. to about 500° C. In one embodiment, reducing occurs under conditions of continuous flow of reducing agent. In one embodiment, the reactor thus subjected to reducing can be afterward kept under positive pressure, or be sealed, with reducing agent and/or inert gas so as to be ready for future use.

In one aspect, the present invention relates to a process for preparing 2,3,3,3-tetrafluoropropene comprising (a) removing impurities from a reactor such that the reactor is substantially free of impurities, (b) providing a starting composition comprising HCFC-244bb in the reactor, and (c) contacting the starting composition in the reactor with a dehydrochlorination catalyst to produce a final composition comprising HFO-1234yf. The step of removing impurities is achieved by (i) purging the reactor with an inert gas, (ii) optionally, oxidizing the impurities in the reactor by introducing an oxidizing agent into the reactor under conditions effective to oxidize the impurities, (iii) reducing the impurities in the reactor by introducing a reducing agent into the reactor under conditions effective to reduce the impurities, (iv) cooling the reactor to an ambient temperature while passing the reducing agent and/or inert gas through the reactor, and (v) maintaining a positive pressure in the reactor with the reducing agent and/or the inert gas.

Additional embodiments and advantages to the present invention will be readily apparent to one of skill in the art, based on the disclosure provided herein.

DETAILED DESCRIPTION OF PREFERRED EMBODIMENTS

According to one embodiment, the present invention relates to a process for removing impurities from a reactor previously exposed to the dehydrohalogenation conversion of HCFC-244bb to HFO-1234yf. The reactor preferably, though not exclusively, comprises an inner metal alloy surface that contains one or more impurities that reduce selectivity to HFO-1234yf. Using one or more of the methods provided herein, the impurities are substantially removed from the reactor, particularly, though not exclusively, during reactor shut-down or maintenance. When the reactor is used in the manufacturing process for making HFO-1234yf using a starting or intermediate material comprising HCFC-244bb, it is substantially free of impurities. Accordingly, the present invention provides methods of removing impurities from the reactor to improve the overall efficiency of the HFO-1234yf conversion process. In certain aspects, the preparation of HFO-1234yf generally includes at least three reaction steps, as follows:

(i) ($CX_2$=CCl—$CH_2$X or $CX_3$—CCl=$CH_2$ or $CX_3$—CHCl—$CH_2$X)+HF→2-chloro-3,3,3-trifluoropropene (HCFO-1233xf)+HCl in a vapor phase reactor charged with a solid catalyst;

(ii) 2-chloro-3,3,3-trifluoropropene (HCFO-1233xf)+HF→2-chloro-1,1,1,2-tetrafluoropropane (HCFC-244bb) in a liquid phase reactor charged with a liquid hydrofluorination catalyst; and (iii) 2-chloro-1,1,1,2-tetrafluoropropane (HCFC-244bb)→2,3,3,3-tetrafluoropropene (HFO-1234yf) in a vapor phase reactor, wherein X is independently selected from F, Cl, Br, and I, provided that at least one X is not fluorine.

The starting material in the first reaction step is one or more chlorinated compounds according to Formulas I, II, and/or III:

$CX_2$=CCl—$CH_2$X    (Formula I)

$CX_3$—CCl=$CH_2$    (Formula II)

$CX_3$—CHCl—$CH_2$X    (Formula III)

wherein X is independently selected from F, Cl, Br, and I, provided that at least one X is not fluorine. In certain embodiments, these compounds contain at least one chlorine, a majority of X is chlorine, or all X is chlorine.

In the first step, the starting composition (which, in certain embodiments comprises 1,1,2,3-tetrachloropropene (HCO-1230xa), 2,3,3,3-tetrachloropropene (HCO-1230xf) and/or 1,1,1,2,3-pentachloropropane (HCC-240db)) reacts with anhydrous HF in a first vapor phase reactor (fluorination reactor) to produce a mixture of at least HCFO-1233xf (2-chloro-3,3,3-trifluoropropene) and HCl. The reaction can be carried out at a temperature of about 200-400° C. and a pressure of about 0-200 psig. The effluent stream exiting the vapor phase reactor may optionally comprise additional components, such as un-reacted HF, un-reacted starting composition, heavy intermediates, HFC-245cb, or the like.

This reaction may be conducted in any reactor suitable for a vapor phase fluorination reaction. The reactor may be constructed from materials which are resistant to the corrosive effects of hydrogen fluoride and catalyst such as Hastalloy, Inconel, Monel. In case of a vapor phase process, the reactor is filled with a vapor phase fluorination catalyst. Any fluorination catalysts known in the art may be used in this process. Suitable catalysts include, but are not limited to chromium, aluminum, cobalt, manganese, nickel and iron oxides, hydroxides, halides, oxyhalides, inorganic salts thereof and their mixtures any of which may be optionally halogenated. Combinations of catalysts suitable for the present invention nonexclusively include $Cr_2O_3$, $FeCl_3/C$, $Cr_2O_3/Al_2O_3$, $Cr_2O_3/AlF_3$, $Cr_2O_3$/Carbon, $COCl_2/Cr_2O_3/Al_2O_3$, $NiCl_2/Cr_2O_3/Al_2O_3$, $CoCl_2/AlF_3$, $NiCl_2/AlF_3$ and mixtures thereof. Chromium oxide/aluminum oxide catalysts are described in U.S. Pat. No. 5,155,082 which is incorporated herein by reference. Chromium (III) oxides such as crystalline chromium oxide or amorphous chromium oxide are preferred with amorphous chromium oxide being most preferred. Chromium oxide ($Cr_2O_3$) is a commercially available material which may be purchased in a variety of particle sizes. Fluorination catalysts having a purity of at least 98% are preferred. The fluorination catalyst is present in an excess but in at least an amount sufficient to drive the reaction.

This first step of the reaction is not necessarily limited to a vapor phase reaction and may also be performed using a liquid phase reaction or a combination of liquid and vapor phases, such as that disclosed in U.S. Published Patent Application No. 20070197842, the contents of which are incorporated herein by reference. It is also contemplated that the reaction can be carried out batch wise, continuous, or a combination of these. For embodiments in which the reaction comprises a liquid phase reaction, the reaction can be catalytic or non-catalytic. Lewis acid catalysts, such as metal-halide catalysts, including antimony halides, tin halides, thallium halides, iron halides, and combinations of two or more of these, may be employed. In certain embodiments, metal chlorides and metal fluorides are employed, including, but not limited to, $SbCl_5$, $SbCl_3$, $SbF_5$, $SnCl_4$, $TiCl_4$, $FeCl_3$ and combinations of two or more of these.

In the second step of the process for forming 2,3,3,3-tetrafluoropropene, HCFO-1233xf is converted to HCFC-244bb. In one embodiment, this step may be performed in the liquid phase in a liquid phase reactor, which may be TFE or PFA-lined. Such a process may be performed in a temperature range of about 70-120° C. and about 50-120 psig.

Any liquid phase fluorination catalyst may be used in the invention. A non-exhaustive list include Lewis acids, transition metal halides, transition metal oxides, Group IVb metal halides, a Group Vb metal halides, or combinations thereof. Non-exclusive examples of liquid phase fluorination catalysts are an antimony halide, a tin halide, a tantalum halide, a titanium halide, a niobium halide, and molybdenum halide, an iron halide, a fluorinated chrome halide, a fluorinated chrome oxide or combinations thereof. Specific non-exclusive examples of liquid phase fluorination catalysts are $SbCl_5$, $SbCl_3$, $SbF_5$, $SnCl_4$, $TaCl_5$, $TiCl_4$, $NbCl_5$, $MoCl_6$, $FeCl_3$, a fluorinated species of $SbCl_5$, a fluorinated species of $SbCl_3$, a fluorinated species of $SnCl_4$, a fluorinated species of $TaCl_5$, a fluorinated species of $TiCl_4$, a fluorinated species of $NbCl_5$, a fluorinated species of $MoCl_6$, a fluorinated species of $FeCl_3$, or combinations thereof. Antimony pentachloride is most preferred.

These catalysts can be readily regenerated by any means known in the art if they become deactivated. One suitable method of regenerating the catalyst involves flowing a stream of chlorine through the catalyst. For example, from about 0.002 to about 0.2 lb per hour of chlorine can be added to the liquid phase reaction for every pound of liquid phase fluorination catalyst. This may be done, for example, for from about 1 to about 2 hours or continuously at a temperature of from about 65° C. to about 100° C.

This second step of the reaction is not necessarily limited to a liquid phase reaction and may also be performed using a vapor phase reaction or a combination of liquid and vapor phases, such as that disclosed in U.S. Published Patent Application No. 20070197842, the contents of which are incorporated herein by reference. To this end, the HCFO-1233xf containing feed stream is preheated to a temperature of from about 50° C. to about 400° C., and is contacted with a catalyst and fluorinating agent. Catalysts may include standard vapor phase agents used for such a reaction and fluorinating agents may include those generally known in the art, such as, but not limited to, hydrogen fluoride.

In the third step of HFO-1234yf production, HCFC-244bb is fed to a second vapor phase reactor (dehydrochlorination reactor) to be dehydrochlorinated to make the desired product 2,3,3,3-tetrafluoropropene (HFO-1234yf). This reactor contains a catalyst that can catalytically dehydrochlorinate HCFC-244bb to make HFO-1234yf.

The catalysts may be metal halides, halogenated metal oxides, neutral (or zero oxidation state) metal or metal alloy, or activated carbon in bulk or supported form. Metal halide or metal oxide catalysts may include, but are not limited to, mono-, bi-, and tri-valent metal halides, oxides and their mixtures/combinations, and more preferably mono-, and bi-valent metal halides and their mixtures/combinations. Component metals include, but are not limited to, $Cr^{3+}$, $Fe^{3+}$, $Mg^{2+}$, $Ca^{2+}$, $Ni^{2+}$, $Zn^{2+}$, $Pd^{2+}$, $Li^+$, $Na^+$, $K^+$, and $Cs^+$. Component halogens include, but are not limited to, $F^-$, $Cl^-$, $Br^-$, and $I^-$. Examples of useful mono- or bi-valent metal halide include, but are not limited to, LiF, NaF, KF, CsF, $MgF_2$, $CaF_2$, LiCl, NaCl, KCl, and CsCl. Halogenation treatments can include any of those known in the prior art, particularly those that employ HF, $F_2$, HCl, $Cl_2$, HBr, $Br_2$, HI, and $I_2$ as the halogenation source.

When neutral, i.e., zero valent, metals, metal alloys and their mixtures are used. Useful metals include, but are not limited to, Pd, Pt, Rh, Fe, Co, Ni, Cu, Mo, Cr, Mn, and combinations of the foregoing as alloys or mixtures. The catalyst may be supported or unsupported. Useful examples of metal alloys include, but are not limited to, SS 316, Monel 400, Inconel 825, Inconel 600, and Inconel 625. Such catalysts may be provided as discrete supported or unsupported elements and/or as part of the reactor and/or the reactor walls.

Preferred, but non-limiting, catalysts include activated carbon, stainless steel (e.g., SS 316), austenitic nickel-based alloys (e.g., Inconel 625), nickel, fluorinated 10% CsCl/MgO, and 10% CsCl/$MgF_2$. A suitable reaction temperature is about 300-550° C. and a suitable reaction pressure may be between about 0-150 psig. The reactor effluent may be fed to a caustic scrubber or to a distillation column to remove the byproduct of HCl to produce an acid-free organic product which, optionally, may undergo further purification using one or any combination of purification techniques that are known in the art.

The reaction may be carried out at a temperature range of from about 200° C. to about 800° C., from about 300° C. to about 600° C., or from about 400° C. to about 500° C. Suitable reactor pressures range from about 0 psig to about 200 psig, from about 10 psig to about 100 psig, or from about 20 to about 70 psig.

In vapor-phase HCFC-244bb dehydrochlorination, HCFC-244bb feed, which can be formed from HCFO-1233xf hydrofluorination as described in US 20090240090, the contents of which are incorporated herein by reference, is fed continuously to a vaporizer and the vaporized feed to a reactor. Due to incomplete conversion of HCFO-1233xf and its close boiling point to HCFC-244bb as well as the formation of azeotrope or azeotrope-like composition of HCFC-244bb and HCFO-1233xf under certain conditions, the separation of these two compounds is difficult. For this reason, the HCFC-244bb feed generally contains certain amount of HCFO-1233xf. The dehydrochlorination reaction may be carried out under conditions to attain a HCFC-244bb conversion of about 5% or higher, about 20% or higher, or about 30% or higher. The reaction may be carried out at a temperature in the range of from about 200° C. to about 800° C., from about 300° C. to about 600° C., or from about 400° C. to about 500° C.; the reactor pressure may be in the range of from about 0 psig to about 200 psig, from about 10 psig to about 100 psig, or from about 20 to about 70 psig.

In general, the effluent from the dehydrochlorination reactor may be processed to achieve desired degrees of separation and/or other processing. Besides HFO-1234yf produced, the effluent generally contains HCl, unconverted HCFC-244bb, and HCFO-1233xf (which is mainly carried over from the previous step of HCFO-1233xf hydrofluorination). Optionally, HCl is then recovered from the result of the dehydrochlorination reaction. Recovery of HCl is conducted by conventional distillation where it is removed from the distillate. Alternatively, HCl can be recovered or removed by using water or caustic scrubbers. When a water extractor is used HCl is removed as an aqueous solution. When a caustic solution is used, HCl is removed from system as a chloride salt in aqueous solution. After the recovery or removal of HCl, the organic stream may be sent to a distillation column for separation. HFO-1234yf, collected from the overhead of the column, may be sent to another column for further purification, while a fraction of the mixture of HCFO-1233xf and HCFC-244bb, accumulated in the reboiler, may be sent back to the dehydrochlorination reactor for the recycle of HCFC-244bb, and the rest to the HCFO-1233xf hydrofluorination reactor for the recycle of HCFO-1233xf.

Applicants have surprisingly discovered that, after one or more cycles of the foregoing, the reactor used in the dehydrochlorination of HCFC-244bb to form HFO-1234yf will contain impurities such as metal halides. Such impurities, if left in the reactor during the next dehydrochlorination cycle, will decrease the selectivity to HFO-1234yf and increase selectivity toward HCFO-1233xf—an undesired byproduct. While not intending to be bound by theory, it is believed that metal halides such as $NiX_2$ (X=F, or Cl) $CrX_3$, $FeX_3$, $MoX_3$, $NbX_3$, $CoX_2$, and the like, are incidentally formed by halogenation of the metal components of the reactor (e.g., Inconel 625). These metal halides, especially trivalent metal halides, act as dehydrofluorination catalysts converting HCFC-244bb to HCFO-1233xf. The present invention provides a solution to this problem by reducing the content of impurities in the reactor during shut-down and/or maintenance of the reactor, thereby improving HFO-1234yf selectivity and similarly reducing the formation of HCFO-1233xf.

To this end, the impurities in the reactor are removed such that the reactor is substantially free of impurities. As used herein, the term "impurities" includes any compound or combination of compounds that reduce the selectivity of HCFC-244bb to HFO-1234yf and/or increase selectivity changeover from HFO-1234yf to HCFO-1233xf. Such impurities may include, but are not limited to, metal halides, metal oxides, and carbonaceous materials. As used herein, the definition of "substantially free" means that the amount of impurities is reduced in the reactor so as to measurably improve selectivity of the conversion of HCFC-244bb to HFO-1234yf and/or decrease selectivity in the conversion of HCFC-244bb to HCFO-1233xf. While the definition of "substantially free" may be as defined herein, in one aspect, the removal of impurities to a "substantially free level" improves selectivity of HCFC-244bb to HFO-1234yf to at least 90% or higher, 95% or higher, or 97% or higher, or 99% or higher, or 99.5% or higher. Selectivity may be calculated by number of moles of product (HFO-1234yf) formed divided by number of moles of reactant consumed or, otherwise, using standard methods known in the art.

The step of removing impurities from the reactor may be accomplished after the dehydrochlorination reaction of HCFC-244bb is discontinued by subjecting the metal alloy reactor to the following treatments: (1) purging the reactor with an inert gas; (2) optionally, oxidizing the impurities in the reactor by introducing an oxidizing agent into the reactor under conditions effective to oxidize the impurities; (3) reducing the impurities in the reactor by introducing a reducing agent into the reactor under conditions effective to reduce the impurities; (4) cooling the reactor to an ambient temperature while passing the reducing agent and/or inert gas through the reactor; and (5) maintaining a positive pressure in the reactor with the reducing agent and/or the inert gas. In certain embodiments the impurities include, but are not limited to, metal halides, metal oxides, and carbonaceous materials. The metal halides may include, for example, halides of Ni, Cr, Fe, Cu, Mo, Nb, and Co.

The inert gas introduced into the reactor in the purging step may include, but is not limited to, He, Ar, $N_2$, and combinations of these. The purging step may be carried out at a temperature range of from about 100° C. to about 700° C., about 200° C. to about 600° C., about 300° C. to about 500° C., or about 400° C. to about 500° C.

The oxidizing agent may be introduced into the reactor under conditions effective to burn off the carbonaceous materials in the reactor. To this end, the oxidizing agent may include, but is not limited to, $H_2O$, $CO_2$, $O_2$, air, $O_3$, $Cl_2$, $N_2O$, and combinations of these. Such oxidizing agents may be pure or diluted with an inert gas such as $N_2$, Ar, and He. In one practice of this embodiment, the oxidizing agent is oxygen and is diluted with nitrogen. The dilution can be as high as practically possible, for example, about 0.1% volume of oxidizing agent. In a preferred embodiment, the concentration of oxidizing agent after dilution ranges from about 0.5 to about 21 vol %, preferably from about 1 to about 5 vol %, and more preferably from about 2 to about 3 vol %. The oxidizing step may be carried out at a temperature range of from about 100° C. to about 700° C., about 200° C. to about 600° C., about 300° C. to about 500° C., or about 400° C. to about 500° C. In another preferred embodiment, air is used as oxygen source and diluted air is used. In yet another preferred embodiment, air is used together with steam in a steam-air decoking process, in which air is used to burn off the carbonaceous materials and steam is used to keep the burning temperatures low such that they do not exceed the maximum tolerable temperatures.

The reducing agent may be introduced into the reactor under conditions effective to convert any metal halides or metal oxides into metallic metals. To this end, the reducing agent may include, but is not limited to, $H_2$, $NH_3$, and $C_1$-$C_{12}$ hydrocarbons. In certain embodiments, the reducing agent is diluted or provided in diluted form. Suitable diluents include inert gases such as $N_2$, Ar, and He. In one practice of this embodiment, the reducing agent is hydrogen and is diluted with nitrogen. The dilution can be as high as practically possible, for example, about 0.1% volume of reducing agent. In a preferred embodiment, the concentration of reducing agent after dilution ranges from about 0.5 to about 20 vol %, preferably from about 1 to about 5 vol %, and more preferably from about 2 to about 2.5 vol %. The reducing step may be carried out at a temperature range of from about 100° C. to about 700° C., about 200° C. to about 600° C., about 300° C. to about 500° C., or about 400° C. to about 500° C.

In certain embodiments, the cooling step is carried out in the presence of an inert gas including, but not limited to, He, Ar, $N_2$, and combinations of these. Similarly, the step of maintaining a positive pressure in the reactor until the next reaction is carried out may be with an inert gas including, but not limited to, He, Ar, $N_2$, and combinations of these. In embodiments in which a reducing agent is used to maintain a positive pressure, the reducing agent may include, but is not limited to, $H_2$, $NH_3$, $C_1$-$C_{12}$ hydrocarbons, and combinations of these. In certain embodiments, the step of maintaining positive pressure in the reactor may be carried out with a reducing agent diluted with an inert gas.

The following are examples of the invention and are not to be construed as limiting.

EXAMPLES

Example 1

This example illustrates the performance of an Inconel 625 reactor which had been used for HCFC-244bb dehydrochlorination for over 1000 hours and exposed to air at room temperature for about two months after shut-down.

The cylindrical Inconel 625 reactor of ¾" diameter was immersed into a 3-zone electrical furnace. Process temperatures were recorded using a multi-point thermocouple placed inside the reactor. A feed containing 99.1 GC area % HCFC-244bb and 0.6 GC area % HCFO-1233xf was fed into the bottom of the vertically mounted reactor and was vaporized before reaching reaction zone. The reaction was conducted under conditions of 480° C., 0 psig, and 12 g-organic/h. Effluent gases were passed through a gas sampling tube so that the progress of the reaction was monitored periodically via GC analysis of the contents of the gas sampling tube. The results show during the period of 10 hours on stream, the averaged HCFC-244bb conversion, HFO-1234yf selectivity, and HCFO-1233xf were 99.7%, 5.3%, and 92.4%, respectively, indicating the un-treated reactor after the initial 1000 hours on stream was more active for HCFC-244bb dehydrofluorination than for dehydrochlorination.

Example 2

This example illustrates the performance of an Inconel 625 reactor which has been used for HCFC-244bb dehydrochlorination for over 1000 hours and treated in hydrogen flow for two hours at 480° C. and then kept in nitrogen (never exposed to air) at room temperature for about two months after shut-down.

The cylindrical Inconel 625 reactor of ¾" diameter is immersed into a 3-zone electrical furnace. Process temperatures are recorded using a multi-point thermocouple placed inside the reactor. A feed containing 99.1 GC area % HCFC-244bb and 0.6 GC area % HCFO-1233xf is fed into the bottom of the vertically mounted reactor and is vaporized before reaching reaction zone. The reaction is conducted under conditions of 480° C., 0 psig, and 12 g-organic/h. Effluent gases are passed through a gas sampling tube so that the progress of the reaction is monitored periodically via GC analysis of the contents of the gas sampling tube. The results show during the period of 10 hours on stream, the averaged HCFC-244bb conversion, HFO-1234yf selectivity, and HCFO-1233xf are 30.0%, 99.5%, and 0.4%, respectively, indicating hydrogen-treated reactor after the initial 1000 hours on stream is more active for HCFC-244bb dehydrochlorination than for dehydrofluorination.

What is claimed is:

1. A process for removing impurities from a reactor comprising an inner metal alloy surface such that the reactor is substantially free of impurities comprising the steps of:
   (a) purging the reactor with an inert gas;
   (b) optionally, oxidizing the impurities in the reactor by introducing an oxidizing agent into the reactor under conditions effective to oxidize the impurities;
   (c) reducing the impurities in the reactor by introducing a reducing agent into the reactor under conditions effective to reduce the impurities;
   (d) cooling the reactor to an ambient temperature while passing the reducing agent and/or inert gas through the reactor; and
   (e) maintaining a positive pressure in the reactor with the reducing agent and/or the inert gas.

2. The process of claim 1, wherein the impurities in the reactor are selected from the group consisting of metal halides, metal oxides, and carbonaceous materials.

3. The process of claim 2, wherein the metal halides comprise halides of Ni, Cr, Fe, Mo, Nb, Cu, or Co.

4. The process of claim 1, wherein the inert gas introduced into the reactor in the purging step comprises a gas selected from the group consisting of He, Ar, $N_2$, and combinations of these.

5. The process of claim 4, wherein the inert gas is $N_2$.

6. The process of claim 4, wherein the purging step is carried out at a temperature of from about 100° C. to about 700° C.

7. The process of claim 4, wherein the purging step is carried out at a temperature of from about 200° C. to about 600° C.

8. The process of claim 4, wherein the purging step is carried out at a temperature of from about 300° C. to about 500° C.

9. The process of claim 4, wherein the purging step is carried out at a temperature of from about 400° C. to about 500° C.

10. The process of claim 2, wherein the oxidizing agent is introduced into the reactor under conditions effective to burn off the carbonaceous materials in the reactor.

11. The process of claim 10, wherein the oxidizing agent introduced into the reactor in the oxidizing step comprises a gas selected from the group consisting of $H_2O$, $CO_2$, $O_2$, air, $O_3$, $Cl_2$, $N_2O$, and combinations of these.

12. The process of claim 11, wherein the oxidizing gas comprises is air.

13. The process of claim 11, wherein the oxidizing step is carried out at a temperature of from about 100° C. to about 700° C.

14. The process of claim 11, wherein the oxidizing step is carried out at a temperature of from about 200° C. to about 600° C.

15. The process of claim 11, wherein the oxidizing step is carried out at a temperature of from about 400° C. to about 500° C.

16. The process of claim 2, wherein the reducing agent is introduced into the reactor under conditions effective to convert any metal halides or metal oxides into metallic metals.

17. The process of claim 16, wherein the reducing agent introduced into the reactor in the reducing step comprises a gas selected from the group consisting of $H_2$, $NH_3$, and $C_1$-$C_{12}$ hydrocarbons.

18. The process of claim 17, wherein the reducing gas is $H_2$.

19. The process of claim 17, wherein the reducing step is carried out at a temperature of from about 100° C. to about 700° C.

20. The process of claim 17, wherein the reducing step is carried out at a temperature of from about 200° C. to about 600° C.

21. The process of claim 17, wherein the reducing step is carried out at a temperature of from about 400° C. to about 500° C.

22. A process for preparing 2,3,3,3-tetrafluoropropene comprising:
  (a) removing impurities from a reactor such that the reactor is substantially free of impurities comprising the steps of:
    (i) purging the reactor with an inert gas;
    (ii) optionally, oxidizing the impurities in the reactor by passing an oxidizing agent through the reactor at a temperature that is sufficiently high to oxidize the impurities;
    (iii) reducing the impurities in the reactor by passing a reducing agent through the reactor at a temperature that is sufficiently high to reduce the impurities;
    (iv) cooling the reactor to an ambient temperature while passing the reducing agent and/or inert gas through the reactor; and
    (v) maintaining a positive pressure in the reactor with the reducing agent and/or the inert gas;
  (b) providing a starting composition comprising 2-chloro-1,1,1,2-tetrafluoropropane in the reactor; and
  (c) contacting the starting composition in the reactor under conditions effective to produce a final composition comprising 2,3,3,3-tetrafluoropropene.

* * * * *